(12) United States Patent
Jovanov et al.

(10) Patent No.: US 9,706,949 B2
(45) Date of Patent: Jul. 18, 2017

(54) SYSTEMS AND METHODS FOR AUTOMATICALLY QUANTIFYING MOBILITY

(71) Applicants: Emil Jovanov, Huntsville, AL (US); Aleksander Milenkovic, Madison, AL (US); Mladen Milosevic, Huntsville, AL (US)

(72) Inventors: Emil Jovanov, Huntsville, AL (US); Aleksander Milenkovic, Madison, AL (US); Mladen Milosevic, Huntsville, AL (US)

(73) Assignee: The Board of Trustees of the University of Alabama, for and on behalf of the University of Alabama in Huntsville, Hunstville, AL (US)

( * ) Notice: Subject to any disclaimer, the term of this patent is extended or adjusted under 35 U.S.C. 154(b) by 157 days.

(21) Appl. No.: 14/192,642

(22) Filed: Feb. 27, 2014

(65) Prior Publication Data
US 2014/0330172 A1 Nov. 6, 2014

Related U.S. Application Data

(60) Provisional application No. 61/770,183, filed on Feb. 27, 2013.

(51) Int. Cl.
*A61B 5/103* (2006.01)
*A61B 5/117* (2016.01)
(Continued)

(52) U.S. Cl.
CPC ......... *A61B 5/1116* (2013.01); *A61B 5/0022* (2013.01); *A61B 5/112* (2013.01);
(Continued)

(58) Field of Classification Search
CPC .... A61B 5/1116; A61B 5/1117; A61B 5/1118; A61B 5/7264; A61B 5/6823;
(Continued)

(56) References Cited

U.S. PATENT DOCUMENTS 5,573,011 A * 11/1996 Felsing .................. 600/595
2004/0015103 A1 * 1/2004 Aminian ............... A61B 5/1116
600/595

(Continued)

OTHER PUBLICATIONS

Van Lummel et al. "Automated approach for quantifying the repeated sit-to-stand using one body fixed sensor in young and older adults", Gait & Posture, vol. 38, pp. 153-156, first available online Nov. 25, 2012.*

(Continued)

*Primary Examiner* — Devin Henson
(74) *Attorney, Agent, or Firm* — Maynard Cooper & Gale, P. C.; Jon E. Holland

(57) ABSTRACT

A system and method for automatically quantifying mobility of a person performing a mobility diagnostic procedure. In one exemplary embodiment, the system measures a posture change test procedure with integrated inertial, location, and navigation type sensors found in a mobile computing device worn by a patient during the posture change test procedure, such as a timed-up-and-go (TUG) procedure. The measurements captured during the posture change inform a health care provider about the mobility of a patient. For example, a determination about the likelihood of the patient experiencing a fall can be assessed from measurable parameters produced from the inertial, location, and navigation-type sensors.

24 Claims, 7 Drawing Sheets

(51) Int. Cl.
*A61B 5/11* (2006.01)
*A61B 5/00* (2006.01)
*G06K 9/00* (2006.01)
*A61B 5/024* (2006.01)

(52) U.S. Cl.
CPC .......... *A61B 5/1121* (2013.01); *A61B 5/6898* (2013.01); *A61B 5/024* (2013.01); *A61B 5/1117* (2013.01); *A61B 5/1118* (2013.01); *A61B 5/1122* (2013.01); *A61B 5/6823* (2013.01); *A61B 5/7264* (2013.01); *A61B 5/7275* (2013.01); *A61B 2503/08* (2013.01); *A61B 2562/0219* (2013.01); *G06K 9/00342* (2013.01); *G06K 9/00348* (2013.01)

(58) Field of Classification Search
CPC .......... A61B 2562/0219; A61B 5/1121; A61B 5/1122; A61B 2503/08; G06K 9/00342; G06K 9/00348; A63B 24/0003; A63B 24/0006; A63B 2024/0071; G08B 21/043; G08B 21/0446

USPC .................................................. 600/587, 595
See application file for complete search history.

(56) References Cited

U.S. PATENT DOCUMENTS

| | | | |
|---|---|---|---|
| 2008/0045804 A1* | 2/2008 | Williams | A61B 5/112 600/300 |
| 2009/0030345 A1* | 1/2009 | Bonnet et al. | 600/587 |
| 2012/0259648 A1* | 10/2012 | Mallon | G06F 19/3418 705/2 |
| 2013/0218053 A1* | 8/2013 | Kaiser et al. | 600/595 |
| 2014/0174174 A1* | 6/2014 | Uehara | A61B 5/227 73/379.01 |

OTHER PUBLICATIONS

Kerr et al. "Analysis of the sit-stand-sit movement cycle in normal subjects", Clinical Biomechanics, vol. 12, No. 4, 1997, pp. 236-245.*

* cited by examiner

Detection of the smartphone orientation.

600

| Parameter | Description | Units |
|---|---|---|
| d.TUG | Total duration of the TUG test | seconds |
| d.S2ST | Total duration of the sit-to-stand transition | seconds |
| d.LF | Duration of the lean forward phase in the sit-to-stand transition | seconds |
| d.LT | Duration of the list phase in the sit-to-stand transition | seconds |
| a.S2ST | Maximum change of the trunk angle in the lean forward phase | degrees |
| v.LF | Maximum angular velocity during the lean forward phase | degrees/s |
| v.LT | Maximum angular velocity during the lift up phase | degrees/s |
| d.ST2S | Duration of the stand-to-sit transition | seconds |
| d.PS | Duration of the prepare-to-sit phase in the stand-to-sit transition | seconds |
| d.SD | Duration of the sit-down phase in the stand-to-sit transition | seconds |

*FIG. 6*

SYSTEMS AND METHODS FOR AUTOMATICALLY QUANTIFYING MOBILITY

CROSS REFERENCE TO RELATED APPLICATION

This application claims priority to U.S. Provisional Patent Application No. 61/770,183, entitled "Smartphone Instrumentation of Timed-Up-and-Go, Balance and Stability Procedures" and filed on Feb. 27, 2013, which is incorporated herein by reference.

STATEMENT REGARDING FEDERALLY SPONSORED RESEARCH OR DEVELOPMENT

This invention was made with Government support under CNS-1205439 awarded by the National Science Foundation. The Government has certain rights in the invention.

RELATED ART

Health care providers often monitor elderly patients to determine the patient's mobility, e.g., their ability to move in multiple directions within a specified time frame. Health care providers use the mobility monitoring of elderly patients to understand and assess the elderly patient's overall health. One such method for monitoring mobility involves an approved diagnostic procedure by the Center for Disease Control (CDC), which measures the duration of a patient transitioning from a sitting-to-standing posture, walking a short distance, and then finally transitioning from a standing-to-sitting posture. This procedure is sometimes termed the "Timed-Up-and-Go" (TUG) procedure. The TUG procedure requires that the patient change his posture and increase his heart rate to perform the task. Conventionally, the TUG procedure is administered by technicians and/or health care providers within a health care facility. The technician often uses a stopwatch to measure the duration of the entire procedure, i.e., from an initial sitting position to a final sitting position.

However, the above described procedure is subjective, manually intensive, and may involve a patient leaving his home to travel to the health care facility. This travel requirement can be a significant inconvenience for patients that have limited travel means, particularly if they depend on family members or public transportation. In addition, human error in timing the TUG procedure may adversely affect the test results.

One conventional system uses a dedicated hardware medical device strapped to the patient in order to measure the movement of the patient via an integrated accelerometer. The accelerometer is used to sense when the patient has (1) initiated the test by sensing a sitting-to-standing posture change and (2) completed the test by sensing a standing-to-sitting posture change. Accordingly, the start and stop times of the test are automatically sensed thereby eliminating human error in the test results. However, the hardware for performing such TUG test can be relatively expensive and may require trained professionals to operate the TUG test, thereby preventing the widespread adoption of the system to administer simple mobility tests.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 6 is a table of other example parameters measured by the mobile computing device during the diagnostic procedure.

DETAILED DESCRIPTION

The present disclosure generally pertains to systems and methods for automatically quantifying mobility of a person performing a mobility test procedure. In one exemplary embodiment, a system measures a posture change test procedure with integrated inertial, location, and navigation type sensors commonly found in a mobile computing device to be worn by a patient during the posture change test procedure, such as the TUG procedure, described earlier. As an example, the mobile computing device may include a gyroscope that is capable of measuring angular movement of a patient during posture changes, such as when the patient transitions from a sitting position to a standing position and from a standing position to a sitting position. The measurements captured during the posture change can inform a health care provider about the mobility of a patient. For example, a determination about the likelihood of the patient experiencing a fall can be assessed from measurable parameters produced from the inertial, location, and navigation-type sensors.

Figure 1:
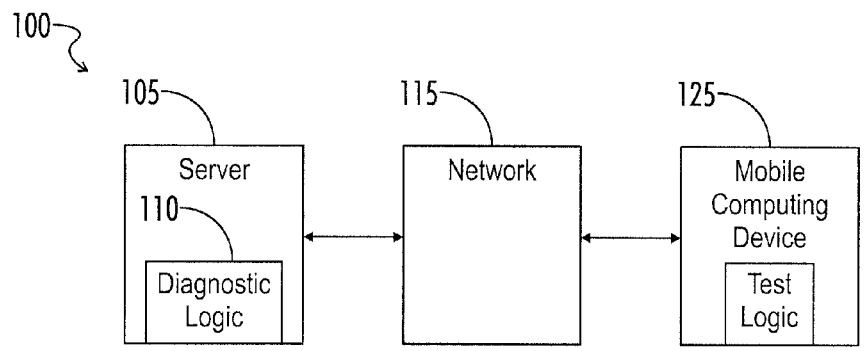
FIG. 1 is a block diagram depicting an exemplary embodiment of a system for use in performing mobility test procedures.

A system 100 for measuring multiple phases of a diagnostic posture change procedure is shown in FIG. 1. The system 100 includes a server 105 configured to store data related to measurements taken during the diagnostic posture change procedure. The server 105 resides geographically apart from the location of the administering of the diagnostic posture change procedure. The server 105 may comprise one or more databases for storing data and results from the diagnostic posture change procedure. Additionally, the server 105 comprises logic 110, referred to herein as "diagnostic logic," that is configured to analyze the stored data related to measurements taken during the diagnostic posture change procedure. In this regard, the diagnostic logic 110 is configured to analyze physiological responses to a person performing the diagnostic posture change procedure along with analyzing extracted mobility-related parameters specific to the diagnostic posture change procedure.

The extracted mobility-related parameters, which are described below in greater detail, are transmitted to the server 105 over a network 115 that is communicatively coupled to the server 105. The network 115 may be, for example, a local area network (LAN) or a wide area network (WAN). As an example, the network 115 may include a WiFi network or the Internet. The network 115 may operate via any one of many communication protocols including, for example, transmission control protocol/Internet protocol (TCP/IP), Ethernet, 802.11a, 802.11b, 802.11g, and 802.11n.

The network 115 is also communicatively coupled to a mobile computing device (MCD) 125. The mobile computing device 125 may be any type of computing device, such as a cellular telephone, a tablet computer, a personal digital assistant (PDA), or a wearable computing device, capable of processing data from one or more sensors, as will be described in more detail below, and communicating data with the network 115. In one exemplary embodiment, the mobile computing device 125 is implemented as a cellular telephone (e.g., a smartphone) and accesses the Internet via a cellular network in order to communicate with the server 105.

A patient or test subject wears the mobile computing device 125 during the course of performing the diagnostic posture change procedure. The mobile computing device 125 acquires the mobility parameters that correlate to the diagnostic posture change procedure via one or more sensors capable of detecting inertia, location, movement, or navigation of the user performing the diagnostic posture change procedure. The mobility parameters correspond to different phases of the diagnostic posture change procedure. For example, the mobility parameters captured by the mobile computing device 125, when worn by the user, can include duration times for one or more completed phases of the diagnostic posture change procedure. Additionally, positional values related to the user's dynamically changing posture, including angular movements, lateral movements, and vertical movements during the course of the diagnostic procedure are also captured by the mobile computing device 125. Specific parameters and positional values are described below with respect to FIG. 6.

The mobile computing device 125 comprises logic 255, referred to herein as "test logic," that is configured to process and quantify mobility-related parameters, such as balance and stability parameters, from which mobility may be assessed. In one embodiment, the balance and stability parameters are in angular units of degrees. Accordingly, the test logic 255 is configured to store measured angular movement and displacement data correlated to the user's mobility at the server 105 or on board the mobile computing device 125 in memory 250 as data 253. Likewise, the test logic 255 is also configured to store measured angular velocity data at the server 105 or on board the mobile computing device 125 in the memory 250.

Figure 2:
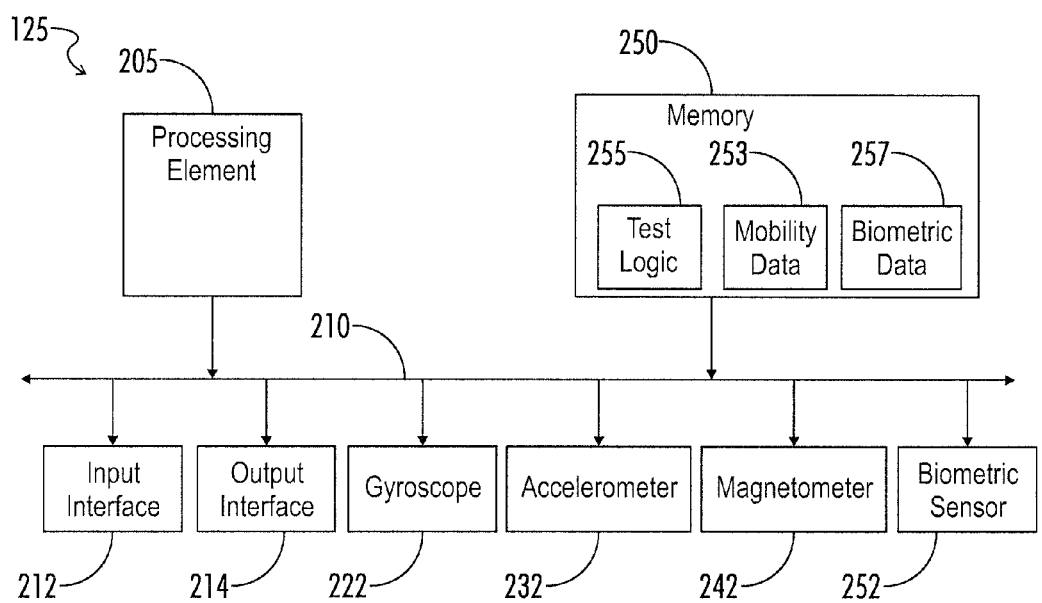
FIG. 2 is a block diagram depicting an exemplary mobile computing device shown in FIG. 1.

FIG. 2 depicts one exemplary embodiment of the mobile computing device 125 comprising a processing element 205. The processing element 205 is configured to drive various components in the mobile computing device 125 via a local interface 210, which may include at least one bus. As an example, the processing element 205 may be a digital signal processor (DSP), central processing unit (CPU), or any instruction execution apparatus that is configured to retrieve and execute instructions from the memory 250.

The local interface 210 is coupled to an input interface 212 and an output interface 214. The input interface 210 comprises one or more devices for receiving inputs from a user, such as a keyboard, a keypad, or a microphone, for example. The output interface 214 comprises one or more devices for providing output to a user, such as a display (e.g., a light emitting diode (LED) display or a liquid crystal display (LCD)) or a speaker. In one exemplary embodiment, the input interface 210 and the output interface 214 are both implemented via a touch screen capable of displaying images to a user while receiving touch-based inputs from a user.

One or more sensors for sensing movement of the mobile computing device 125 are coupled to the local interface 210. In one exemplary embodiment, the sensors include a gyroscope 222, an accelerometer 232, and a magnetometer 242, but other types of sensors may be used in other embodiments, such as a biometric sensor 252. The gyroscope 222 is used for detecting and measuring angular movements of the mobile computing device 125 and, hence, the user when the mobile computing device 125 is strapped or otherwise attached to the user. Specifically, the gyroscope 222 measures three-dimensional angular velocity of rotation. In this regard, the gyroscope 222 measures rotation around an x-axis, a y-axis (which is orthogonal to the x-axis), and a z-axis (which is orthogonal to both the x-axis and the y-axis). Further discussion about the mobile computing device's orientation when it is worn by a user is described more fully below.

The accelerometer 232 is used for automatically counting the number of steps a user walks during the TUG procedure. The accelerometer 232 measures translational movements of the user by sensing x, y, and/or z components of the user's acceleration while wearing the mobile computing device 125. In this regard, each step that user takes increases the acceleration measured by the accelerometer 232. In one example, the highest measured acceleration occurs during the end of a "swing" phase of the user's step, i.e. as the user swings his leg in motion to complete his step. Generally, the test logic 255 is configured to interpret the accelerometer measurements for a given time period as a step provided that the measurements for such time period fit an expected step profile (e.g., a period of increased acceleration measurements between periods of decreased acceleration measurements). Thus, over time, the test logic 255 based on measurements by the accelerometer 232 may count the number of steps that the user makes while performing the diagnostic procedure.

The magnetometer 242 is used for automatically sensing changes of direction by the user during the TUG procedures. In this regard, the magnetometer 242 is configured to sense a magnitude of the Earth's magnetic field and to convert the magnetic field measurement into a directional heading. That is, the magnetometer 242 functions as a compass to indicate the directional orientation of the magnetometer 242 and, hence, the device 125. Based on the directional heading indicated by the magnetometer 252, the test logic 255 is configured to determine when the user has turned, such as when the user completes his walk and turns around to prepare to sit. Such input may be useful for determining when the user has completed or is about to initiate a particular phase of the diagnostic procedure. The magnetometer 252 also may be used to detect smaller rotational movements associated with the user, such as when walking in slight side-to-side movements indicative of an unsteady walk.

Note that many conventional smartphones incorporate a gyroscope 222, accelerometer 232, and magnetometer 242. Thus, when the MCD 125 is implemented as a smartphone, it may be unnecessary to separately purchase or equip the MCD 125 with these types of sensors. Any of the sensors may be integrated with or communicatively coupled to the MCD 125. As an example, when the MCD 125 is strapped to a chest of a patient, the biometric sensor 252 may be attached to the strap and communicate with the test logic 255 via a wired or wireless connection. Other arrangements are possible in other embodiments.

The biometric sensor 252 is used for automatically detecting physiological characteristics or traits that correspond to one or more parts of the body, including iris, retina, skin, odor, gait, and heart, for example. In this regard, the biometric sensor 252 is configured to measure or capture the existence of a trait pertaining to an area of the human body. In one embodiment, the biometric sensor 252 is configured to measure a heart rate of the patient, but other types of biometric sensors 252 may be used in other embodiments. Herein, the acquisition of the trait by the biometric sensor 252 can be used to determine parameters that exist at a particular time, based on an identifiable phase or transition within the TUG procedure.

As shown by FIG. 2, mobility data 253 indicative of the readings from the gyroscope 222, the accelerometer 232, the magnetometer 242, and the biometric sensor 252 is stored in memory 250. The mobility data 253 is derived from each of the aforementioned sensors reflecting automatically measured parameters associated with movement of the mobility computing device 125 when worn by the user during a diagnostic procedure. As an example, while the user is performing a diagnostic procedure, such as the TUG procedure, the test logic 255 is configured to store as part of the mobility data 253 sample readings from the gyroscope 222, accelerometer 232, and magnetometer 242 and to correlate with each sample a timestamp indicative of the time of the sample's occurrence. Also, the test logic 255 may be configured to calculate various mobility parameters based on the stored readings and store the calculated parameters in memory 250 as part of the mobility data 253.

In the exemplary embodiment shown by FIG. 2, the test logic 255 is implemented in software and stored in the memory 250. In other embodiments, the test logic 255 may be implemented in firmware, software, hardware, or any combination thereof. Note that the diagnostic logic 105 may be similarly implemented in firmware, software, hardware, or any combination thereof. When implemented in software, the test logic 255 and/or diagnostic logic 105 can be stored and transported on any computer-readable medium for use by or in connection with an instruction execution apparatus that can fetch and execute instructions. In the context of this document, a "computer-readable medium" can be any means that can contain or store code for use by or in connection with the instruction execution apparatus.

As will be described in more detail hereafter, the test logic 255 is configured to detect various phases of the TUG procedure, such as the beginning of the sit-to-stand transition, based on the mobility data 253. For example, the logic 255 is configured to analyze the mobility data 253 to identify phases and events within the diagnostic procedure, such as when the user begins the TUG procedure, when the user has leaned forward to stand, when the user has completed a sit-to-stand transition, when the user is walking, when the user initiates a stand-to-sit transition, and when the user has completed the stand-to-sit transition. Moreover, based on the mobility data 253, the test logic 255 automatically determines the duration of the entire TUG procedure, thereby avoiding human error that would otherwise occur by a user attempting to manually start and stop a timer for the TUG procedure.

In addition, by identifying phases within the TUG procedure, the test logic 255 may be configured to calculate or otherwise determine various parameters indicative of the user's mobility in addition to the test's duration. As an example, the test logic 25 may determine the amount of time that it takes the user to lean forward in initiating a sit-to-stand transition noting that such duration may be an indicator of mobility. In this regard, it is generally expected that a person with greater mobility is likely to complete such transition in a shorter time. In addition, when the test logic 255 determines that the user is walking, the test logic 255 may analyze the readings of the magnetometer 242 or gyroscope 222, for example, to determine the extent to which there is side-to-side or rotational movement during a procedure. More side-to-side or rotational movement while walking may indicate decreased stability and higher probability of fall.

In one exemplary embodiment, the test logic 255 uses mobility data 253 captured by the gyroscope 222 or magnetometer 242 to determine an amount or rate of sway that the user exhibits during his walking phase in the TUG procedure. For example, the gyroscope 222 or magnetometer 242 may detect the user's angular movement in a horizontal plane during a phase of the TUG procedure, such as the walking phase. In this regard, after identifying the walking phase in the captured sensor data, the test logic 255 analyzes the sensor data from the gyroscope 222 or magnetometer 242 for such phase in order to calculate or otherwise provide a value indicative of the extent to which the patient sways or moves from side-to-side. Thereafter, the test logic 255 may use such value to calculate a value indicative of the patient's mobility, such as the mobility indicator or the fall probability indicator described herein.

In another exemplary embodiment, the test logic 255 uses biometric data 257, detected by the biometric sensor 252, to determine when the captured biometric data 257 aligns with identified transitions and phases of the TUG procedure. For example, when the biometric sensor 252 measures heart rate, the test logic 255 determines the heart rate measurement at the beginning of the sit-to-stand transition, during the leaning forward phase, and at the end of the sit-to-stand transition, when the user stands upright. Note that each sample from a given sensor (including the gyroscope 222, the accelerometer 232, the magnetometer 242, and the biometric sensor 252) is correlated with a timestamp indicative of the time that the sample was measured. These timestamps may be used to correlate a particular measurement from the biometric sensor 252 with a particular posture transition.

As an example, to better assess the patient's health, it may be desirable to know the change in the patient's heart rate for the sit-to-stand transition. In such case, the test logic 255 is configured to identify a measurement of the biometric sensor 252 that occurred at the point of transition from the leaning forward phase to the lift-up phase and also to identify another measurement of the biometric sensor 252 that occurred during sit-to-stand transition. The test logic 255 then subtracts the two measurements to determine the rate of change in the patient's heart rate during the transition. The test logic 255 may be configured to use measurements from the biometric sensor 252 in order to calculate a health indicator indicative of the patient's health similar to the techniques described herein for calculating a mobility indicator.

Note that the test logic 255 may be configured to compare measurements from one diagnostic procedure to the next in order to provide a mobility, fall probability, or health indicator. As an example, the test logic 255 may assess the degree to which a particular parameter, such as an angular velocity, angle, or biometric parameter, at a particular point in the diagnostic procedure changes over time and then use such calculated change to determine trends of changes in mobility, fall probability, or health indicator. As an example, the test logic 255 may determine how much the heart rate measurement described above for the lift-up phase changes over time and use such rate of change to calculate a health indicator indicative of the likelihood of the patient experiencing a deterioration of an acute condition, such as heart attack or viral infection. Alternatively, the test logic 255 may determine how much the maximum angular velocity or angle measured by the gyroscope 222 during the leaning forward phase (or some other phase) changes over time and use such rate of change to calculate a mobility indicator or a fall probability indicator.

Accordingly, the test logic 255 uses the identified events and phases to determine various parameters, including biometric and movement-related parameters, which are indicative of mobility and health, so that a better assessment of mobility and health can be ascertained.

In one exemplary embodiment, the logic 255 is configured to calculate or otherwise determine a mobility indicator indicative of the user's overall mobility based on the various mobility parameters calculated or otherwise determined by the test logic 255 in analyzing the measurements from sensors, such as the gyroscope 222, the accelerometer 232 and the magnetometer 242, during the TUG procedure. That is, the mobility indicator is an overall assessment of the user's mobility using various mobility parameters as factors. As an example, the duration of the TUG procedure may be combined with other mobility parameters derived from the TUG procedure to provide a mobility indicator that is a better assessment of the user's actual mobility relative to the duration of the TUG procedure alone. Note that the mobility parameters may be weighted so that a parameter deemed to be a more significant indicator of mobility has a greater effect on the overall assessment.

If desired, the test logic 255 may be configured to upload the mobility data 253, including the sensor measurements and/or the mobility parameters determined by the test logic 255, to the server 105 via the network 115. The diagnostic logic 110 or test logic 255 is configured to analyze the results of multiple tests over time in an effort to assess how the user's mobility changes over time. The diagnostic logic 110 or test logic 255 is also configured to parse the mobility data 253 for presentation to one or more users, such as health care providers, at locations remote from the mobile computing device 125. As an example, the mobile computing device 125 may be used at a patient's home, and the results sent to a health care facility where health care providers can review the results. Note that FIG. 1 shows the test logic 255 implemented at the mobile computing device 125 and the diagnostic logic 110 implemented at the server 105. However, other locations of the logic 255 and 110 are possible. For example, it is possible for portions of the test logic 255 to be implemented at the server 105 or other location and for portions of the diagnostic logic 110 to be implemented at the mobile computer device 125 or other location.

Figure 3:
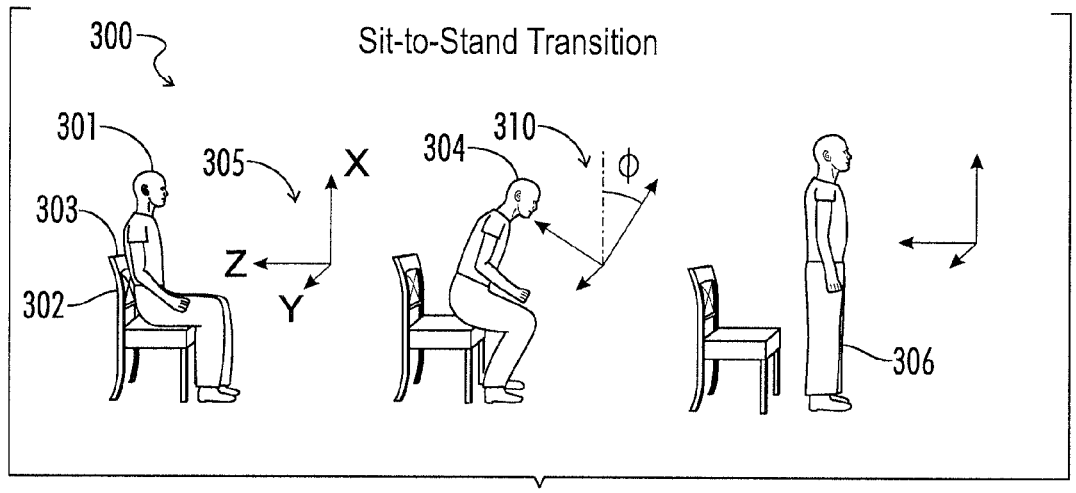
FIG. 3 is a pictorial diagram depicting a conventional sitting-to-standing transition conducted as a diagnostic procedure.

FIG. 3 depicts an illustration of a sitting-to-standing transition 300 that an individual subject or patient 301 performs as at least part of a diagnostic procedure, such as the TUG procedure described earlier. The subject 301 initially sits erect in a straight-back chair 303, thereby forming a sitting position 302. As shown by FIG. 3, the subject 301 may keep his back as straight, his feet flat on the ground, his hands on his upper legs, and his head straight, while looking forward. A reference orientation 305 is shown in FIG. 3 to depict the three-dimensions that can be used to describe movements of the subject 301. In the depicted illustration 300, the reference orientation 305 includes a vertical axis (x), a lateral axis (y), and a sagittal axis (z).

As the subject 301 leans forward prior to rising from the chair 303, the subject transitions during a phase, referred to herein as the "leaning forward phase," from the position 302 to a leaning forward position prior to rising from the chair 303. As the user leans forward, the subject's chest rotates from the vertical axis by an angle, $\theta$. The leaning forward phase is assumed to last until the user's chest reaches a maximum angle $\theta_{max}$, which typically occurs just before the subject 301 rises from the chair 303 to stand, thereby starting the next phase, referred to herein as the "lift-up phase," where the subject 301 rises to a standing position 306. That is, during the leaning forward phase, the subject 301 undergoes a change in his upper body angle relative to an upright position where the angle, $\theta$, changes from approximately 0 degrees in the upright position 302 to some maximum angle, $\theta_{max}$. Thus, an angular displacement 310 of $\theta_{max}$ occurs while the subject 301 moves within the leaning forward phase. Subsequently, in the lift-up phase, the subject 301 rises from the chair 303 and stands erect in the standing position 306. Thus, $\theta_{max}$ marks the end of the leaning forward phase and the beginning of the lift-up phase. The end of the leaning forward phase is also characterized by the angular velocity approaching close to zero. While the user is transitioning from the leaning forward position to a standing position, the subject's chest rotates back toward its original position that existed before the leaning forward phase. It is generally expected that the chest of a healthy or mobile person will rotate back to approximately 0 degrees (fully erect) in the lift-up phase, although the subject's chest rotation may stop sooner. Once the angular rotation in the lift-up phase stops, it is assumed that the lift-up phase ends. Accordingly, when the subject 301 performs the sitting-to-standing transition 300 during a diagnostic procedure, several different phases comprise the sitting-to-standing transition 300, including a sitting down phase, a leaning forward phase, and a lift-up phase.

During a TUG procedure, the subject 301 begins a phase, referred to herein as the "walking phase," after the lift-up phase. In the walking phase, the subject 301 walks to specified point, returns to the chair 303, and then turns around in order to return to the position 306 for sitting down. The subject 301 then initiates a transition from the standing position 306 to the sitting position 302. In performing the transition, the subject's chest rotates to a maximum angle, $\theta_{max}$, during a phase referred to herein as the "preparing-to-sit phase." Then, the subject's chest rotates from this maximum angle to a minimum angle (e.g., close to 0) in a phase referred to herein as the "sitting down phase," at which point the subject is approximately back into the sitting position 302 marking the end of the TUG procedure. The entire time from the point that the subject 301 begins leaning forward from the sitting position 302 and then returns to the sitting position 302 represents the entire duration of the TUG procedure.

Figure 4:
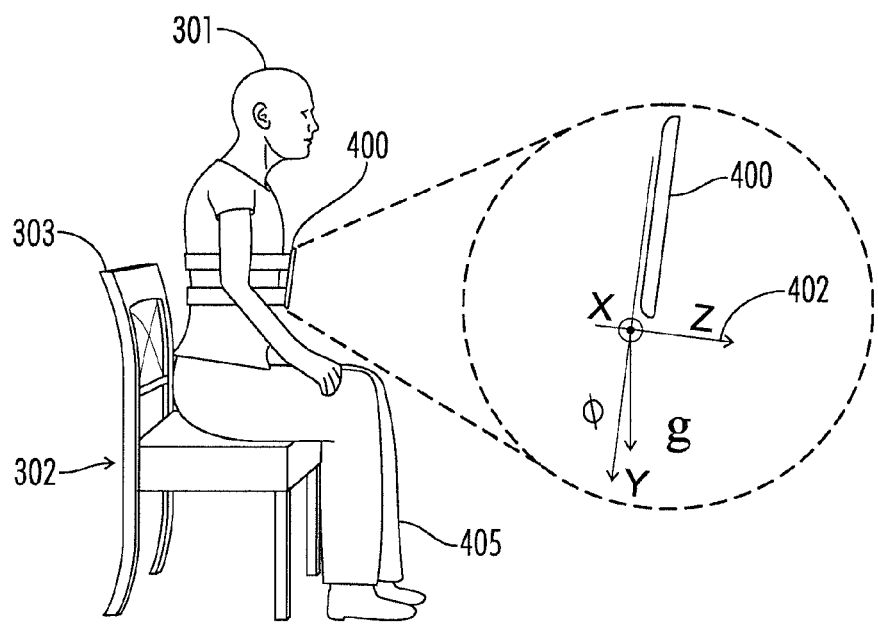
FIG. 4 is a pictorial diagram depicting a user wearing a mobile computing device during a diagnostic procedure.

In one exemplary embodiment, the subject 301 straps or otherwise attaches a mobile computing device 400 to his upper chest and trunk, as shown in FIG. 4. Hereinafter, when the subject 301 wears the mobile computing device 400, he is referred to as user 405. Accordingly, FIG. 4 depicts the user 405 seated in the chair 303 facing forward as described above. In this example, the mobile computing device 400 is implemented as a smartphone, but the mobile computing device 400 could also be another type of computing device, such as a tablet computer, for example. The mobile computing device 400 is positioned proximate to the upper chest of the subject 301 in a predetermined orientation 402 relative to at least one axis, such as the x-axis, y-axis, and z-axis, for example. In this regard, the mobile computing device's z-axis corresponds to the anteroposterior axis, (i.e., from front to back of the user 405). The y-axis corresponds to the dorsoventral axis (i.e., extending along the axis joining the dorsal (back) and ventral (belly) sides). Whereas the x-axis corresponds to the lateral axis of the subject's body (a position farther from the median plane or midline of the body).

As described earlier, the accelerometer 232 is used to measure acceleration of the user 405. That is, the accelerometer 232 detects x, y, and z components of the acceleration of the subject's upper trunk. In the same vein, the gyroscope 222 measures angular displacement of the user 405. Specific angular measurements include rotation around the x-axis, y-axis, and z-axis. Based on the gyroscopic measurements, the test logic 255 can compute angular velocity corresponding to the subject's movements. The logic 255 identifies transitions between specific posture change phases, based on the detected angular displacement and angular velocity, as well as other data sensed by the sensors of the device 400. As an example, in one exemplary embodiment, the logic 255 automatically identifies a transition from the leaning forward phase to the lift-up phase, based on sensor data from at least one of the sensors described herein.

The test logic 255 is configured to analyze the mobility data 253 for certain profiles, also referred to herein as "signatures," of certain events in order to identify transitions from one phase to another. As an example, the test logic 255 may analyze the sensor data from the gyroscope 222 in order to identify the beginning and end of the leaning forward phase so that a point of transition from the leaning forward phase to the lift-up phase can be identified.

Figure 5:
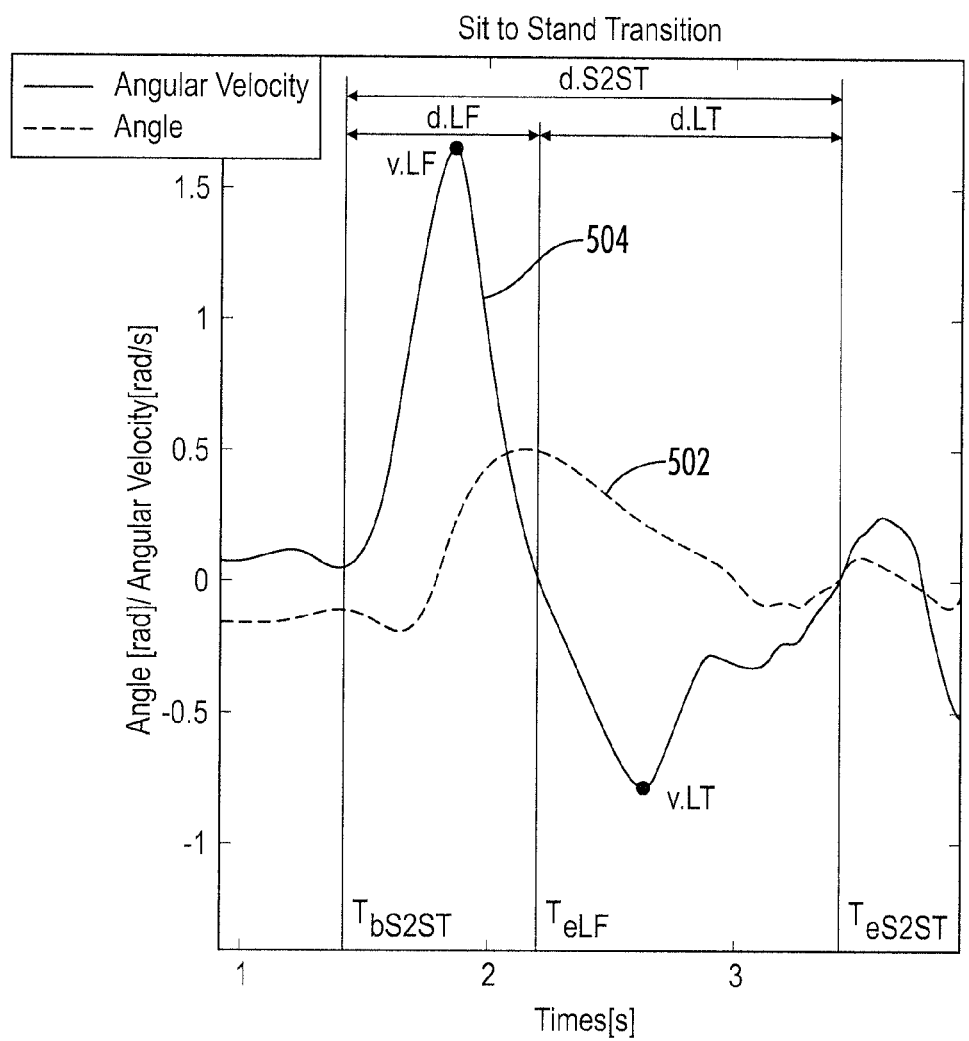
FIG. 5 is a graphic depiction of two example parameters measured by the mobile computing device during the diagnostic procedure.

FIG. 5 graphically depicts exemplary angular measurements from the gyroscope 222 as the user 405 transitions from a sitting position to a standing position. A curve 502, referred to herein as "upper body trunk angle profile," indicates the angle, θ, sensed by the gyroscope 222 during the transition, and a curve 504, referred to herein as "angular velocity profile," indicates the angular velocity indicated by the angular measurements from the gyroscope 222 over the same time period. The upper body trunk angle profile 502 reaches its maximum point at or about the end of the leaning forward phase. Also, the angular velocity is expected to be close to zero at the end of the leaning forward phase. In this regard, at the beginning of the leaning forward phase, the angular velocity increases from approximately 0 to a maximum value (v.LF) and then falls back close to 0 as the angular displacement reaches a maximum ($\theta_{max}$). At this point, the user 405 has leaned forward and is now ready to stand. As the user 405 begins to stand, he begins to rotate his upper body back in the opposite direction thereby decreasing θ as he stands.

The test logic 255 detects the beginning of the sit-to-stand transition 500 and, hence, the start of the TUG procedure by searching for a change in the angular velocity around the lateral axis (i.e., the x component of the gyroscope 122). The change in the angular velocity corresponds to the user 405 beginning to lean forward as he prepares to stand. The test logic 255 initially finds the maximum angular velocity (v.LF) and then searches backward to find the beginning of the slope, which is noticeable when the angular velocity is above a predetermined threshold. As described above, the leaning forward phase ends when the angular velocity returns to approximately zero ($T_{eLF}$), which should approximately coincide with the upper body trunk angle profile 502 reaching its maximum trunk angle in the leaning forward phase. The logic 255 determines the duration of the leaning forward phase as the time between the beginning of the sit-to-stand transition 500 and the end of the leaning forward phase (d.LF=$T_{eLF}-T_{bTUG}$).

The lift-up phase starts at the end of the leaning forward phase and continues until the user 405 reaches a standing position. During the lift-up phase, the user's upper body rotates in a direction opposite to the direction of rotation for the leaning forward phase as he returns his upper body back to an erect posture. Thus, the angular velocity is expected to fall below zero to a maximum negative value (v.LT) at which point the rate of angular displacement change should slow until the user's upper body comes close to rest indicating that the user is now fully erect in the standing position. At such position, the angular velocity should return to approximately zero. The logic 255 is configured to identify the point at which the angular velocity approximately reaches 0 after v.LT as the end of the lift-up phase and, therefore, the end of the sit-to-stand transition 500.

Based on the timestamps for the measurements at the beginning of the leaning forward phase and the end of the lift-up phase, the test logic 255 is configured to determine the duration of the sit-to-stand transition 500 by calculating (d.S2ST=d.LF+d.LT). While the aforementioned description has primarily focused on the sit-to-stand transition 500, another transition in the TUG procedure, i.e., the stand-to-sit transition, can also provide distinct angular velocity and upper body angle trunk angle profiles, based on the user 405 moving through defined posture change phases. The stand-to-sit transition has a preparing-to-sit phase and a sitting down phase that are similar to the lift-up phase and the leaning forward phase in reverse, respectively.

A table 600 of non-exhaustive quantitative parameters that the logic 255 determines is depicted in FIG. 6. The table 600 includes duration times in seconds, angles in degrees, and angular velocities in degrees/seconds. Table 600 includes the total duration of the TUG procedure (d.TUG) and other duration times that the logic 255 determines, such as the total duration of the sit-to-stand transition (d.S2ST), and the total duration of the stand-to-sit transition (d.ST2S). The timing of individual phases are determined by the logic 255 in order to provide greater detail about sit-to-stand transition, including two specific phases, i) the leaning forward phase (d.LF) and ii) the lift-up phase (d.LT). The logic 255 determines the maximum trunk angle (a.S2ST) during the leaning forward phase, the maximum angular velocities in the leaning forward phase (v.LF), and the lift-up phase (v.LT). As stated above, the logic 255 also determines the duration of individual phases of the stand-to-sit transition, a preparing-to-sit phase (d.PS), and a sitting down phase (d.SD).

Figure 7:
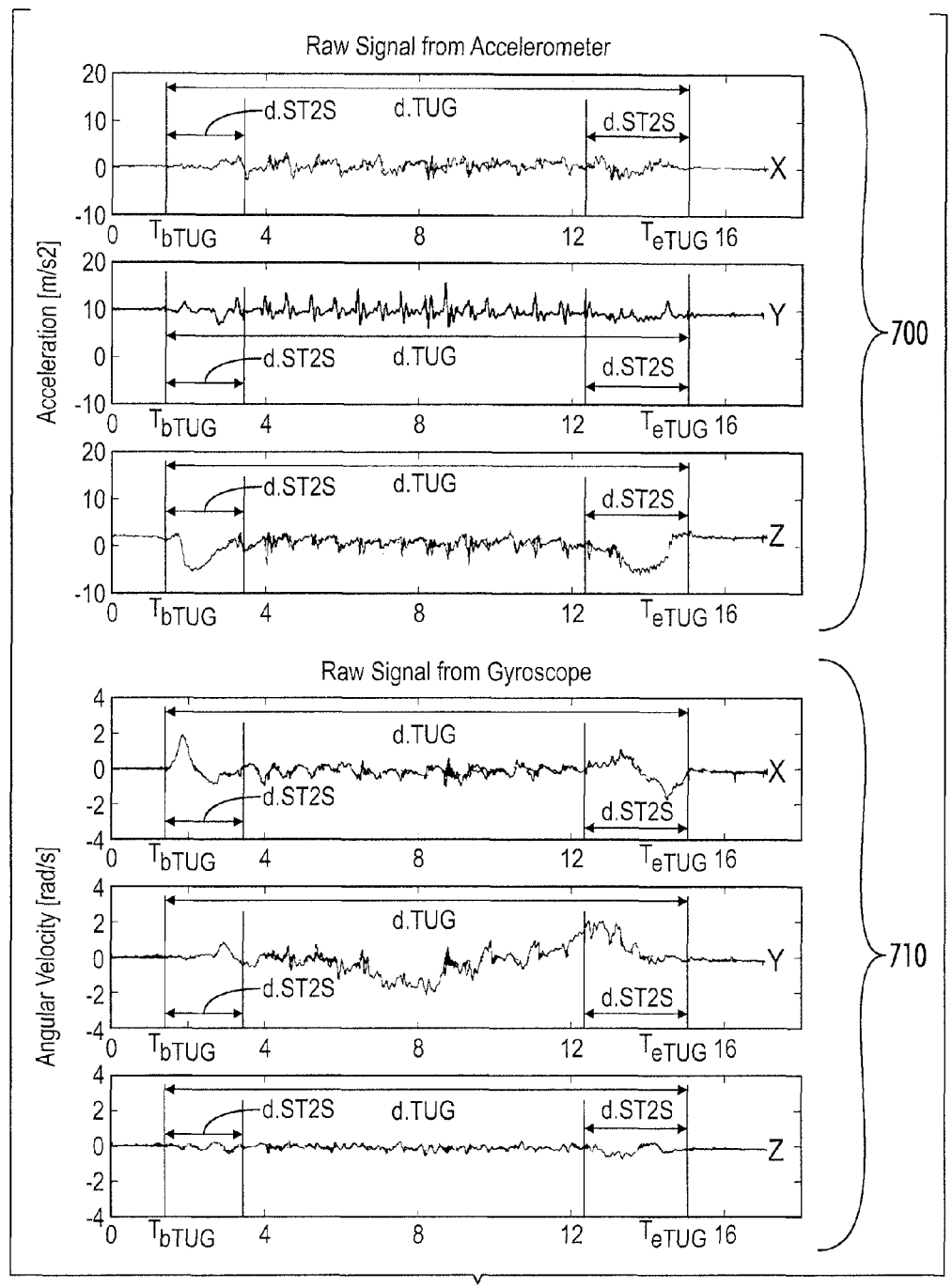
FIG. 7 depicts two example signal graphs of the user's movement during the diagnostic procedure.

The test logic 255 is configured to process raw sensor data detected by sensors, such as the gyroscope 222 and the accelerometer 232, and to extract various quantitative parameters indicative of mobility. FIG. 7 depicts two exemplary raw sensor signals. First, a graph 700 indicative of a raw accelerometer signal is shown, based on recorded data from a user 405 wearing the mobile computing device 125 during a TUG diagnostic procedure. The raw acceleration signal graph 700 comprises x, y, and z signal components that span the duration of the TUG procedure (d.TUG), and acceleration measured in meters/second squared (m/s$^2$). As described earlier, the TUG procedure includes at least three posture transitions corresponding to the user's performance that are also shown in the raw accelerometer signal graph

700. The initial sit-to-stand transition (d.S2ST) includes the beginning of the TUG procedure ($T_{bTUG}$). The middle portion of the TUG procedure includes detected steps as sensed by the accelerometer 232. The final portion of the TUG procedure and the third portion of the raw accelerometer signal graph 700 includes the stand-to-sit transition (ST2S), which marks the end of the TUG procedure ($T_{eTUG}$).

Second, a graph 710 indicative of a raw gyroscope signal is also shown in FIG. 7, based on recorded data from the user 405 wearing the mobile computing device 125 during the TUG diagnostic procedure. The raw gyroscope signal graph 710 comprises x, y, and z signal components that span the duration of the TUG procedure (d.TUG), and angular velocity measured in radians/second (rad/s). Three posture transitions corresponding to the user's performance during the TUG procedure also are reflected in the raw gyroscope signal graph 710. The initial sit-to-stand transition (d.S2ST) includes the beginning of the TUG procedure (TbTUG). The middle portion of the TUG procedure includes movement by the user 405, including steps as sensed by the accelerometer above. The final portion of the TUG procedure and the third portion of the raw gyroscope signal graph 710 includes the stand-to-sit transition (ST2S), which marks the end of the TUG procedure (TeTUG).

The extracted parameters described above provide health care personnel with valuable data and information beyond the conventional timed duration of the user 405 completing the TUG procedure. For example, one or more of the extracted parameters indicate the user's overall mobility and also the user's probability of falling. Therefore, a mobility indicator and a fall probability indicator can be derived in equations that factor in one or more of the extracted parameters, such as angle movement and angular velocity, for example. In one embodiment, the fall probability indicator provides a precise indicator of the user 405 falling, which may be based on factors and/or weights different than those used for the mobility indicator.

As an example, the algorithm for calculating the mobility indicator may be focused on the amount of time the user 405 takes to complete various phases of the TUG procedure. In such algorithm, the duration of one phase, such as the leaning forward phase, may be weighted more than another phase, such as the lift-up phase. However, the algorithm may take into account other factors, such as the degree to which the user 405 moves from side-to-side about the y-axis as he is walking (as determined by the gyroscope 222 or the magnetometer 242, or other sensor configured to detect mobility of the user) and/or the number of steps detected in the walking phase. In this regard, more steps in the walking phase may indicate less mobility, and the algorithm may change the mobility indicator in order to indicate decreased mobility for a higher number of steps. The algorithm may also take into account various other event-based parameters, such as the maximum angle or angular velocity detected in the leaning forward phase. In this regard, it may be observed that users who perform the leaning forward phase quicker or who achieve a larger angle in the leaning forward phase generally have greater mobility. In such case, the algorithm may change the mobility indicator to indicate greater mobility if a greater angle or angular velocity is detected in the leaning forward phase. In other examples, other types of factors may be used to calculate the mobility indicator.

As a mere example, the test logic 255 may calculate the mobility indicator by multiplying the duration of each phase to a respective weight that is predefined and then summing the results. Also, the indicator may be adjusted (e.g., increased or decreased) based on certain events, such as the number of steps detected in the walking phase and/or the maximum angle and/or maximum angular velocity detected for a certain phase, such as the leaning forward phase. As mobility factors are learned, the algorithm for calculating the mobility indicator can be adjusted in an effort to improve the indicator's accuracy.

The fall probability indicator may be calculated from the same or different set of mobility parameters used for calculating the mobility indicator. However, any parameter may be weighted differently in the algorithm for calculating the fall probability indicator relative to the mobility indicator. As an example, if it is determined that side-to-side movement during walking is a significant indicator of a fall, such side-to-side movement may be weighted more in the algorithm for calculating the fall probability indicator.

In one embodiment, the test logic 255 is configured to determine a value indicative of the extent to which the patient shuffles his feet while walking in the walking phase or at other times and to use the value to calculate the mobility indicator or fall probability indicator. In this regard, a person who shuffles his feet may have a different step profile, as measured by the accelerometer 232 or other sensor, and the extent to which the patient shuffles his feet may be quantified based on such profile. In addition, to provide a better estimation of this value, it may be desirable use a sensor (e.g., an accelerometer) positioned on the patient's leg or foot. Such sensor may be configured to communicate wirelessly with the MCD 125 using Bluetooth or some other short-range wireless protocol, although other techniques for communicating with the MCD 125 are possible. As an example, the sensor may be conductively coupled to the MCD 125 so that wireless communication is not necessary. Note that the biometric sensor 252 or other sensor may be configured to communicate with the MCD 125 in the same way if the sensor is not integrated with the MCD 125.

In one embodiment, the diagnostic logic 110 or test logic 255 is configured to correlate efficacy of medical and rehabilitative treatment administered to the user, based on the quantified mobility of the user. In this regard, health care personnel track the user's rehabilitation process by monitoring several daily measurements that have been stored at the server 105 of one or more of the posture change diagnostic procedures described herein. The health care personnel can analyze developed trends relating to when medicine and other types of treatment are given to the user and the user's mobility indicator based on the logic 255 identifying posture change transitions during the diagnostic procedure.

As an example, the server 105 may be configured to receive input indicating when the user 405 takes a certain medication and then correlate the mobility indicators (or other mobility parameters) determined by the test logic 255 with time values relative to the dosage time of the medication. Thus, the mobility data 252 can be analyzed to determine the effect of the medication on the user's mobility over time. As an example, assume that a number of TUG tests are performed each hour after a dosage of medication is administered to the user 405. In such example, the diagnostic logic 110 or test logic 255 is configured to correlate the mobility indicator from each procedure with a time value indicating the amount of time that elapsed from the time that the user 405 took the medication to the time that the procedure was performed. The results of measurements for many dosages can be averaged and interpolated in order to define a set of data that is statistically more accurate.

In one exemplary embodiment, the test logic 255 captures changing physiologic parameters over a prescribed period of time and the diagnostic logic 110 or test logic 255 assesses the user's gait and instability. For example, if the user's maximum angle in the leaning forward phase becomes progressively smaller over time, the diagnostic logic 110 or test logic 255 is configured to determine that the probability of a fall by the user is increasing. Additional assessments may include measuring the symmetry of walking steps taken during the diagnostic procedure.

If desired, the mobile communication device 125 can be used to capture various physiological data, such as heart rate. For example, data from the biometric sensor 252 may be captured by the test logic 255 over time based on the phases detected by the test logic 255. As an example, each time the test logic 255 detects a transition from a sitting position to a standing position, the test logic 255 may be configured to store in the biometric data 257 a sample from the sensor 252. The diagnostic logic 110 or test logic 255 may be configured to monitor the samples to detect changes in the user's condition. As an example, the logic 110 or 255 may compare the user's heart rate detected by the biometric sensor 252 for each sit-to-stand transition and quantify a dynamic response of the user's heart rate respective to performing the posture transition. Changes in the dynamic response may be a predictor or forewarning of a heart attack or some other cardiac ailment or condition. For example, the diagnostic logic 110 or test logic 255 may be configured to analyze a significant increase of heart rate as an indication of good heart health.

The diagnostic logic 110 or test logic 255 may also determine user's health condition from the biometric data 252, which includes the user's gait as sensed by a gait monitor, i.e., a type of biometric sensor 257. In this regard, if the user shuffles his feet more than usual over a period of hours or begins to shuffle his feet at a particular time of day, the diagnostic logic 110 or test logic 255 may determine the onset of a serious medical condition. In short, the diagnostic logic 110 or test logic 255 assesses the user's stride length and symmetry of his steps as detected by the gait monitor, which may be strapped or attached to the user's leg. The gait assessment, conducted by logic 110 or 255, also determines the effectiveness of rehabilitation or therapeutic treatment of the user as the user walks several times during the day or over the course of other periods, including minutes, hours, and months, for example.

Figure 8:
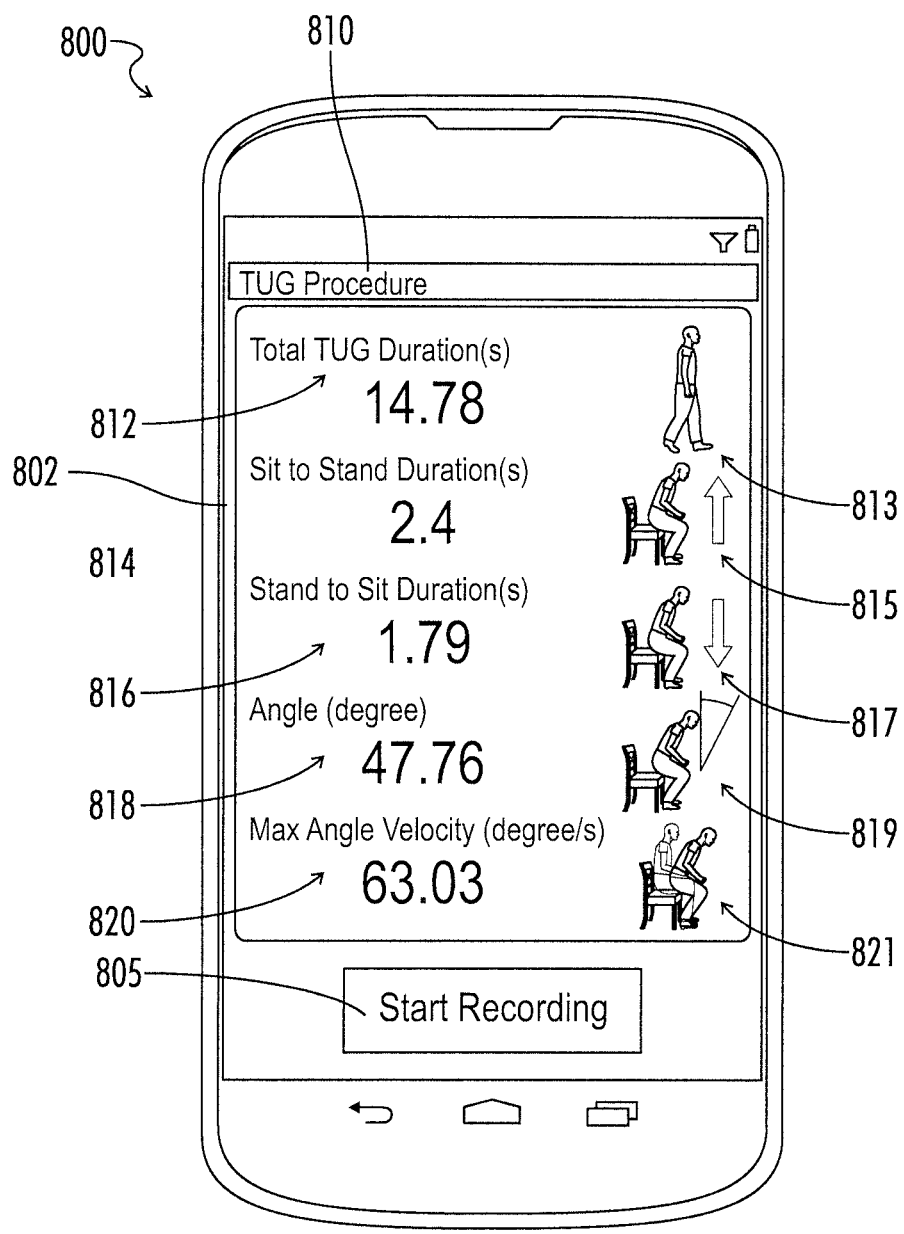
FIG. 8 is a pictorial diagram of the mobile computing device as a smartphone.

An example MCD 125 is shown in FIG. 8. The MCD 125 is illustratively depicted as a smartphone 800. The smartphone 800 comprises a display touch screen 801 displaying a graphical user interface (GUI) 802 for engaging in an automated application run by logic 255. The GUI 802 includes, for example, a record button 805 for initiating the start of the posture change procedure that the user will perform. In one exemplary embodiment, the user performs the TUG procedure described earlier that comprises at least a sit-to-stand transition and a stand-to-sit transition. Therefore, the example smartphone application in FIG. 8 includes a diagnostic procedure notification 810, which informs the user of the type of diagnostic procedure the user will engage in and the smartphone logic 255 will monitor. In the example shown, the TUG procedure is listed in the notification status bar of the display screen 801.

The display screen 801 is further parsed to provide additional information to the user, including aspects about several phases of the TUG procedure. For example, the test logic 255 determines and displays a total duration count 812 on one side of the display screen 801. Across from the total duration count 812, the logic 255 displays a graphical animation 813 of a person walking. Below the total duration count 812, the logic 255 displays a sit-to-stand duration count 814. The corresponding graphical animation 815 depicts a person rising from a sitting position and an "up" arrow.

The logic 255 also displays the stand-to-sit transition count 816 and its corresponding animation 817, which depicts a person preparing to sit along with a "down" arrow. Other useful displayed information includes the detected upper body trunk angle 818 of the user and the corresponding angle animation 819, which depicts a person leaning forward and an angle symbol. The maximum angle velocity count 820 is depicted below the upper body trunk angle 818. A moving animation 821 corresponds to maximum angle velocity count 820. The moving animation 821 depicts a person starting from an upright sitting position and ending in a leaning forward position. In addition, if desired, the mobility indicator and the falling probability indicator may be displayed.

Figure 9:
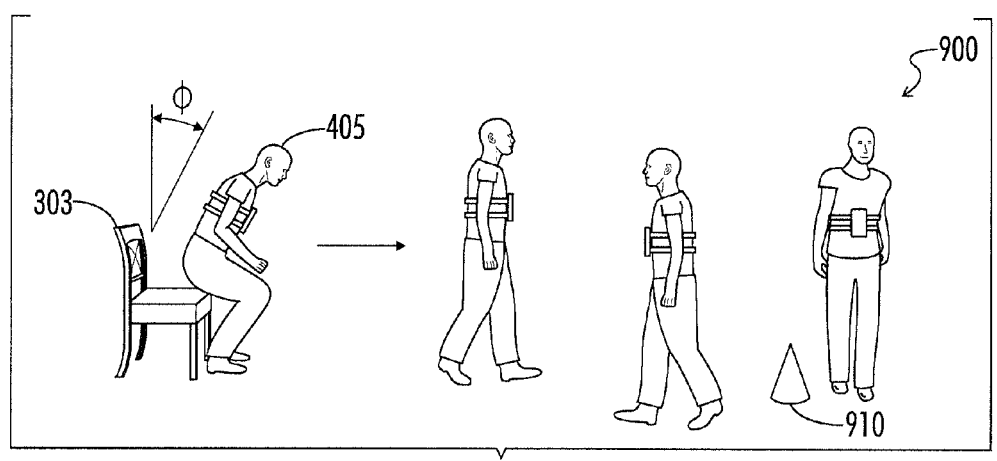
FIG. 9 is a pictorial diagram of example animation for use on the smartphone in FIG. 8.

Several other different graphical methods may be used to depict the information shown in FIG. 8 related to the diagnostic procedure implemented as a smartphone application. For example, in FIG. 9, another graphical depiction of the user 405 performing at least a portion of the diagnostic procedure is illustrated. Accordingly, the user 405 is depicted as leaning forward from a sitting position, while rising. The user stands and begins to walk towards a cone 910. The user walks around the cone before returning to the chair 303.

While the above discussion and extracted parameters have been related to the TUG procedure, other types of posture change tests are contemplated for implementation as software applications with the mobile computing device 125. The test logic 255 is configured to process raw sensor data as measured by integrated sensors within the mobile computing device 125 and correlate the sensor data to identify multiple posture phases. Specifically, the mobile computing device 125 is not limited to quantifying mobility parameters for transitions between sitting positions to standing positions, and the mobile computing device 125 may be used for other types of posture changes.

Note that transitions from one phase to another may be instantaneous or there may be a delay, referred to herein as "transition delay," which itself may be a parameter indicative of mobility that may be used to calculate a mobility or fall probability indicator. As an example, after reaching a maximum angle during the leaning forward phase, the patient may pause momentarily before beginning to stand. Thus, there is a transition delay between the end of the leaning forward phase and the beginning of the lift-up phase, and this delay can be measured. Similarly, after reaching the standing position, the patient may pause before beginning to walk such that a transition delay exists between the end of the lift-up phase and the beginning of the walking phase when the user takes his first step. The transition delay between any two consecutive phases may be measured and used in a calculation of a parameter indicative of mobility or fall probability.

In various embodiments described above, the mobile computing device 125 is described as operating with a gyroscope 222, accelerometer 232, and magnetometer 242. Such sensors are commonly found in conventional smartphones thereby facilitating implementation of the device 125 at a relatively low cost. In this regard, a conventional smartphone can be configured to implement the mobile computing device 125 described herein by merely downloading the test logic 255 to the smartphone without having to purchase or add any additional hardware. However, if desired other types of sensors may be used, and it is unnecessary for a smartphone to be used for implementing the mobile communication device 125.

Now, therefore, the following is claimed:

1. A system for automatically quantifying mobility of a user when the user is performing a mobility diagnostic procedure whereby the user transitions from a sitting position to a standing position, wherein the diagnostic procedure includes a leaning forward phase whereby the user leans to a leaning forward position prior to standing, followed by a lift-up phase whereby the user transitions from the leaning forward position to the standing position, the system comprising:
- at least one sensor for sensing angular movement of the user, the at least one sensor configured to provide sensor data indicative of the angular movement;
- a processing element for executing logic, the logic configured to automatically identify, based on the sensor data, a transition from the leaning forward phase to the lift-up phase and to quantify, based on the sensor data, at least one first mobility parameter for the user during the leaning forward phase and at least one second mobility parameter for the user during the lift-up phase, the logic further configured to determine and display a mobility indicator indicative of the mobility of the user based on the at least one first mobility parameter and the at least one second mobility parameter; and
- wherein the at least one first mobility parameter is indicative of angular movement of the user during the leaning forward phase and is indicative of a duration of the leaning forward phase, wherein the at least one second mobility parameter is indicative of angular movement of the user during the lift-up phase and is indicative of a duration of the lift-up phase, and wherein the logic is configured to determine the mobility indicator by summing the duration of the leaning forward phase multiplied by a first weight and the duration of the lift-up phase multiplied by a second weight that is different than the first weight.

2. The system of claim 1, wherein the at least one first mobility parameter further includes one of a group of parameters including: a maximum angle during the leaning forward phase or a maximum angular velocity during the leaning forward phase, and wherein the at least one second mobility parameter further includes a maximum negative angular velocity during the lift-up phase.

3. The system according to claim 1, wherein the logic is configured to correlate efficacy of medical treatment administered to the user based on the quantified at least one first mobility parameter for the user and at least one second mobility parameter for the user.

4. The system according to claim 1, wherein the logic is configured to determine an indicator indicative of falling probability for the user based on at least one of a group of parameters including: duration of the leaning forward phase, transition duration of the identified transition, a maximum angle during the leaning forward phase, and a maximum angular velocity during the leaning forward phase.

5. The system according to claim 1, wherein the at least one sensor for sensing angular movement of the user is a gyroscope.

6. The system of claim 1, wherein the at least one sensor is configured to measure an upper body angle of the user.

7. The system of claim 1, further comprising a biometric sensor for sensing a biometric parameter of the user, wherein the logic is configured to correlate a measurement from the biometric sensor with the identified transition and to calculate a health indicator for the user based on the correlated measurement.

8. The system of claim 1, further comprising a cellular telephone having the sensor and the logic.

9. The system of claim 1, wherein the logic is configured to determine a value indicative of an extent to which the user shuffles at least one foot during the mobility diagnostic procedure, and wherein the mobility indicator is based on the value.

10. The system of claim 1, further comprising a display screen configured to display, to the user, information about the leaning forward phase and the lift-up phase of the mobility diagnostic procedure.

11. The system of claim 10, wherein the display screen is configured to display, to the user, a graphical user interface, the graphical user interface includes a button to initiate the mobility diagnostic procedure in response to a selection of the button by the user.

12. The system of claim 1, comprising:
- a second sensor for sensing translational movement of the user, the second sensor configured to provide second sensor data indicative of the translational movement; and
- a third sensor for sensing a directional heading of the user, the third sensor configured to provide third sensor data indicative of the directional heading,
- wherein the logic is configured to determine the mobility indicator based on the second sensor data and the third sensor data.

13. The system of claim 12, wherein the logic is configured to determine a value indicative of an extent to which the user shuffles at least one foot during the mobility diagnostic procedure based on the second sensor data, and wherein the logic is further configured to determine the mobility indicator based on the value.

14. The system of claim 1, wherein the logic is configured to determine a third mobility parameter corresponding to the duration of the transition from a sitting position to a standing position based on the duration of the leaning forward phase and the duration of the lift-up phase, the logic further configured to determine the mobility indicator based on the third mobility parameter.

15. The system of claim 1, wherein the logic is configured to adjust the mobility indicator in response to one or more events associated with the mobility diagnostic procedure, the one or more events include at least one of a group of parameters including: maximum angle during a phase of the mobility diagnostic procedure, a number of detected steps during a phase of the mobility diagnostic procedure, and a maximum angular velocity during a phase of the mobility diagnostic procedure.

16. The system of claim 1, wherein the at least one sensor is configured to sense side-to-side movement of the user during a phase of the mobility diagnostic procedure, and wherein the logic is configured to adjust the mobility indicator in response to the sensing of side-to-side movement of the user.

17. A system for automatically quantifying mobility of a user performing a mobility diagnostic procedure, the system comprising:
- a sensor worn by a user during a mobility diagnostic procedure, the sensor configured to detect an upper body angle of the user;
- a processing element for executing logic, the logic configured to identify, based on data from the sensor, a plurality of phases of a transition by the user from a sitting position to a standing position for the mobility diagnostic procedure, the logic configured to detect a change of the upper body angle to identify at least a first phase and a second phase of the plurality of phases during the transition from the sitting position to the standing position, the logic further configured to quantify a plurality of mobility parameters for the user at different phases of the transition based on the data from the sensor, wherein the plurality of mobility parameters includes at least one first mobility parameter for the user during the first phase of the plurality of phases and at least one second mobility parameter for the user during the second phase of the plurality of phases, wherein the at least one first mobility parameter indicates a duration of the first phase, wherein the at least one second mobility parameter indicates a duration of the second phase, wherein the logic is configured to determine the mobility indicator by summing the duration of the first phase multiplied by a first weight and the duration of the second phase multiplied by a second weight that is different than the first weight, and wherein the logic is further configured to display, to the user, a mobility indicator indicative of the mobility of the user based on the quantified plurality of mobility parameters.

18. The system according to claim 17, wherein the first phase includes a leaning forward phase whereby the user leans from the sitting position to a leaning forward position prior to standing, the second phase includes a lift-up phase whereby the user transitions from the leaning forward position to the standing position, wherein the logic is configured to automatically identify, based on the data from the sensor, a transition from the leaning forward phase to the lift-up phase, the logic further configured to determine the mobility indicator based on the identified transition.

19. The system according to claim 18, wherein the logic is configured to identify a maximum angular velocity for the upper body angle during the leaning forward phase, and wherein the mobility indicator is based on the maximum angular velocity.

20. The system according to claim 18, wherein the logic is configured to identify a maximum value of the upper body angle during the leaning forward phase, and wherein the mobility indicator is based on the maximum value.

21. The system according to claim 17, further comprising a magnetometer for detecting a directional heading of the user, and wherein the logic is configured to identify at least one of the phases based on the magnetometer.

22. The system according to claim 17, wherein the sensor is a gyroscope.

23. A method for automatically quantifying mobility of a user when the user is performing a mobility diagnostic procedure whereby the user transitions from a sitting position to a standing position, wherein the diagnostic procedure includes a leaning forward phase whereby the user leans to a leaning forward position prior to standing, followed by a lift-up phase whereby the user transitions from the leaning forward position to the standing position, the method comprising:

sensing angular movement of the user via a sensor attached to the user;

automatically identifying a transition from the leaning forward phase to the lift-up phase and quantifying at least one first mobility parameter for the user during the leaning forward phase and at least one second mobility parameter for the user during the lift-up phase by analyzing sensor data from the sensor for a profile of an event in the mobility diagnostic procedure, wherein the at least one first mobility parameter is indicative of angular movement of the user during the leaning forward phase and is indicative of a duration of the leaning forward phase, and wherein the at least one second mobility parameter is indicative of angular movement of the user during the lift-up phase and is indicative of a duration of the lift-up phase;

determining a mobility indicator indicative of the mobility of the user based on the at least one first mobility parameter and the at least one second mobility parameter, wherein the determining comprises summing the duration of the leaning forward phase multiplied by a first weight and the duration of the lift-up phase multiplied by a second weight that is different than the first weight; and displaying the mobility indicator to the user on an output interface.

24. The method of claim 23, wherein the at least one first mobility parameter further includes one of a group of parameters including: a maximum angle during the leaning forward phase or a maximum angular velocity during the leaning forward phase, and wherein the at least one second mobility parameter further includes a maximum negative angular velocity during the lift-up phase.

* * * * *